United States Patent [19]
Dixon et al.

[11] Patent Number: 5,192,980
[45] Date of Patent: Mar. 9, 1993

[54] APPARATUS AND METHOD FOR METHOD FOR SPATIALLY- AND SPECTRALLY-RESOLVED MEASUREMENTS

[75] Inventors: Arthur E. Dixon, 41 Lane Crescent, Kitchener, Ontario, Canada, N2K 1P2; Savvas Damaskinos, Kitchener; John W. Bowron, Waterloo, both of Canada

[73] Assignee: A. E. Dixon, Waterloo, Canada

[21] Appl. No.: 721,282

[22] Filed: Jun. 26, 1991

[30] Foreign Application Priority Data

Jun. 27, 1990 [GB] United Kingdom ............... 9014263

[51] Int. Cl.⁵ .................... G01J 3/18; G01J 3/26; G01N 21/64
[52] U.S. Cl. .................... 356/326; 356/318; 356/328; 356/334; 356/346; 250/458.1
[58] Field of Search ............... 356/301, 317, 318, 326, 356/328, 346, 381, 382, 334; 250/458.1, 459.1, 461.1, 461.2

[56] References Cited

U.S. PATENT DOCUMENTS 4,844,617 7/1989 Kelderman et al. ............... 356/328

Primary Examiner—F. L. Evans

[57] ABSTRACT

A scanning optical microscope or mapping system for spectrally-resolved measurement of light reflected, emitted or scatttered from a specimen is disclosed, in which the spectrally-resolving element is integrated into the detection arm of the microscope or mapping system to result in good photon collection efficiency as well as good spectral and spatial resolution. A confocal version of the microscope is disclosed which will be of particular interest in fluorescence microscopy, and the non-confocal mapping system will be of particular interest in photoluminescence mapping of semiconductor wafers.

8 Claims, 9 Drawing Sheets

APPARATUS AND METHOD FOR METHOD FOR SPATIALLY- AND SPECTRALLY-RESOLVED MEASUREMENTS

TECHNICAL FIELD

This invention relates to the fields of scanning optical microscopy, photoluminescence analysis and photoluminescence imaging, fluorescence analysis and fluorescence imaging, as well as many other fields, including photon scattering experiments used to map subsurface defects in semiconductor wafers, and Raman Effect measurements.

BACKGROUND OF THE INVENTION

Photoluminescence analysis and photoluminescence imaging are particularly valuable for characterizing semiconductor materials, wafers, epitaxial layers, and devices. In photoluminescence analysis, most measurements to date have been made at a single point on a specimen, especially when the specimen is held at low temperature in a Dewar. Because the signal strength is low, considerable effort has been made to increase the throughput of the grating spectrometer, including a method to shape the beam from the laser (or other light source) at the point of impingement on the specimen so that the illuminated area has the same shape as the entrance slit of the grating monochromator, and when imaged on the entrance slit, slightly overfills it, but provides for very efficient collection of the photoluminescence light produced by the specimen, as described by Gerry Auth in U.S. Pat. No. 4,572,668.

Spectrally-resolved photoluminescence mapping of semiconductor wafers with high spatial resolution has recently been described by Tajima, "Characterization of Semiconductors by Photoluminescence Mapping at Room Temperature", Journal of Crystal Growth 103, 1–7 (1990); by Moore et al, "A Spatially Resolved Spectrally Resolved Photoluminescence Mapping System", Journal of Crystal Growth 103, 21–27 (1990); and in Waterloo Scientific Inc. Application Notes on Photoluminescence #1 (1989) and #2 (1990), Waterloo Scientific Inc., 419 Phillip St., Waterloo, Ont. Canada N2L 3X2. In this application it is known to use apparatuses which are essentially scanning-stage non-confocal laser microscopes, in which the exciting laser wavelength is blocked in the detector path, and the remaining light collected from the specimen is focussed on the entrance slit of a grating spectrometer, which is used to measure the wavelength and intensity of the photoluminescence signal at each specimen position. In this situation, the highest spatial resolution is achieved when the focused spot at the point of impingement on the specimen is as small as possible. The technique of shaping the spot described above reduces the spatial resolution, and is therefore not appropriate when the highest possible spatial resolution is required.

In the field of fluorescence microscopy, the confocal microscopes and techniques presently in use have recently been described in "The Handbook of Biological Confocal Microscopy", IMR Press, Madison, Wiss. (1989), edited by Pawley, and in a review paper by Shotton, "Confocal Scanning Optical Microscopy and its Applications for Biological Specimens", Journal of Cell Science 94, 175–206 (1989). Since there may be more than one source of fluorescence at the focal spot of the confocal microscope, it is important to be able to separate the different wavelengths of the two sources. In addition, a particular fluorescence source may emit different wavelengths, and/or intensities, depending on its local environment, so it is important to be able to map changes in spectra with position in the specimen.

In both photoluminescence and fluorescence, it is known that measurement of lifetimes is important. Photoluminescence or fluorescence decay is usually measured using a pulsed or modulated light source, and the decay of the fluorescence or photoluminescence signal is monitored with a high speed detector. In many cases, more than one lifetime signal is detected, and those signals are mixed together in the detected signal. It is important to be able to separate these lifetimes, and good spatial resolution is also important. In the case of fluorescence measurements, fluorescence recovery after bleaching is also important. In all of these cases, high spectral and spatial resolution in the instrument used to make the measurements, as well as good photon collection efficiency, are important.

A simple prior art confocal scanning laser microscope is shown in FIG. 1. In this implementation the beam from laser 102 is focused by lens 104 on pinhole 106, and the light passing through the pinhole passes through beamsplitter 108 and is focused by objective lens 110 to a focal spot 111 which is diffraction-limited at the surface of (or inside) specimen 112. Light reflected from or emitted by the specimen at focal spot 111 is collected by objective lens 110, and part of this light is reflected by beamsplitter 108 to be focused at detector pinhole 114, which is confocal with focal spot 111 at the specimen and pinhole 106. Light passing through detector pinhole 114 is collected by detector 116. The combination of detector pinhole 114 and detector 116 is a confocal detector. Light from focal spot 111 at specimen 112 passes through detector pinhole 114, but light from any other point on the specimen runs into the edges of detector pinhole 114, and is not collected. Thus, out-of-focus signals are rejected. This gives the confocal microscope the ability to do optical tomography, which allows it to record true three dimensional images. The microscope shown in FIG. 1 uses scanning stages 118 to move the specimen under the stationary laser beam to record the image, but it is also possible to scan the beam instead of scanning the specimen. Microscopes using infinity-corrected optics are also common, both with scanning stages and in scanning-beam configurations. These configurations are described in "The Handbook of Biological Confocal Microscopy" edited by pawley. In addition, detector pinhole 114 and detector 116 behind it can be replaced by a small detector whose area is the same as that of detector pinhole 114.

Confocal Scanning Laser Microscopes have been used to record photoluminescence and fluorescence images with high spatial resolution (in three dimensions) using filters to block the exciting wavelength, but accepting all (or substantially all) wavelengths of the luminescence signal. One possible prior art configuration for such a microscope is shown in FIG. 2, where dichroic beamsplitter 200 transmits light at the wavelength of the incoming laser beam but reflects most of the longer wavelength photoluminescence or fluorescence emitted from specimen 112 towards detector pinhole 114. To further reduce the small amount of reflected laser light, blocking filter 202 which blocks light at the laser wavelength can be placed in the detection arm of the microscope, as shown.

Three known implementations of a confocal microscope that can measure spectrally-resolved data are as follows. It is known that a bandpass filter can be placed in the detection arm of the microscope, either in front of or behind the detector pinhole as described by Stelzer in "Considerations on the intermediate optical system in confocal microscopes", a chapter in "The Handbook of Biological Confocal Microscopy", edited by Pawley. This may allow the operator to separate the emission bands of two fluorophores by using two different bandpass filters, or to measure a crude spectrum by changing filters each time a new wavelength is to be measured, but this technique is impractical for measuring a complete spectrum with good spectral resolution.

A second known implementation is to focus the light emitted from the detector pinhole of a confocal photoluminescence or fluorescence microscope onto the entrance slit of a grating monochromator (or to place the monochromator in a position such that it's entrance slit replaces the detector pinhole). These solutions both pas to the detector only a fraction of the photoluminescence light collected by the microscope, and are expensive because a complete grating monochromator is required.

A third known implementation uses a lens to focus light from the detector pinhole onto the input aperture of a Fourier Transform Infrared Spectrometer, or any other type of spectrometer that is appropriate for the wavelength range involved.

Presently, the simplest confocal fluorescence microscopes usually use a dichroic beamsplitter to separate the longer fluorescence wavelengths from the exciting wavelength, and detect all of the fluorescence wavelengths at once (one such microscope is shown in FIG. 2). This implementation does not allow the operator to make spectrally-resolved measurements.

The present non-confocal photoluminescence mapping system sold by Waterloo Scientific Inc. works by focusing the light from the non-confocal microscope onto the entrance slit of a grating monochromator, which is expensive, and all of the light collected by the objective lens does not reach the grating of the monochromator.

An object of this invention is to provide a scanning microscope or mapping system that has both good spatial resolution and good spectral resolution, and at the same time is very efficient in collecting light emitted from the specimen.

A further object of this invention is to reduce the cost of the spectrally-resolved microscope or mapping system by integrating the spectrally-resolving element into the detection arm of the microscope.

DESCRIPTION OF THE INVENTION

We have invented a spectrally-resolved confocal scanning optical microscope that incorporates one or more of a class of generalized confocal microscopes. The present invention is a microscope with good spatial resolution and good spectral resolution and is very efficient at collecting light from the specimen. This is achieved by integrating a monochromator or spectrometer (several kinds are possible) into the detection arm of a confocal microscope, in front of the detector pinhole. In the case of a confocal fluorescence or photoluminescence microscope, this allows the confocal properties of the microscope to be maintained while providing an efficient light path for detecting spatially-resolved fluorescence or photoluminescence spectra. Non-confocal implementations are also disclosed.

The invention can be implemented in several ways. First, several embodiments will be described in which a grating has been added to scanning laser microscopes of various optical designs to form an integrated monochromator. In this embodiment, the illuminated spot on the specimen acts like the entrance aperture of the integrated grating monochromator. (A prism monochromator could also be integrated into the microscope in a similar way.) The scanning laser microscope is used for illustration only. Any instrument that measures spectra resulting from excitation of the specimen by a focused beam of radiation (or two focused beams that are confocal, or a focused and an unfocused beam) could benefit from the invention.

Next, embodiments will be described in which the grating is replaced by spectrometers using interference effects, including, but not necessarily limited to, Fabry Perot interferometers and Fourier Transform spectrometers. In these cases the exciting beam need not be focused, since the illuminated spot on the sample does not act as an entrance aperture for these devices.

Figure 1:
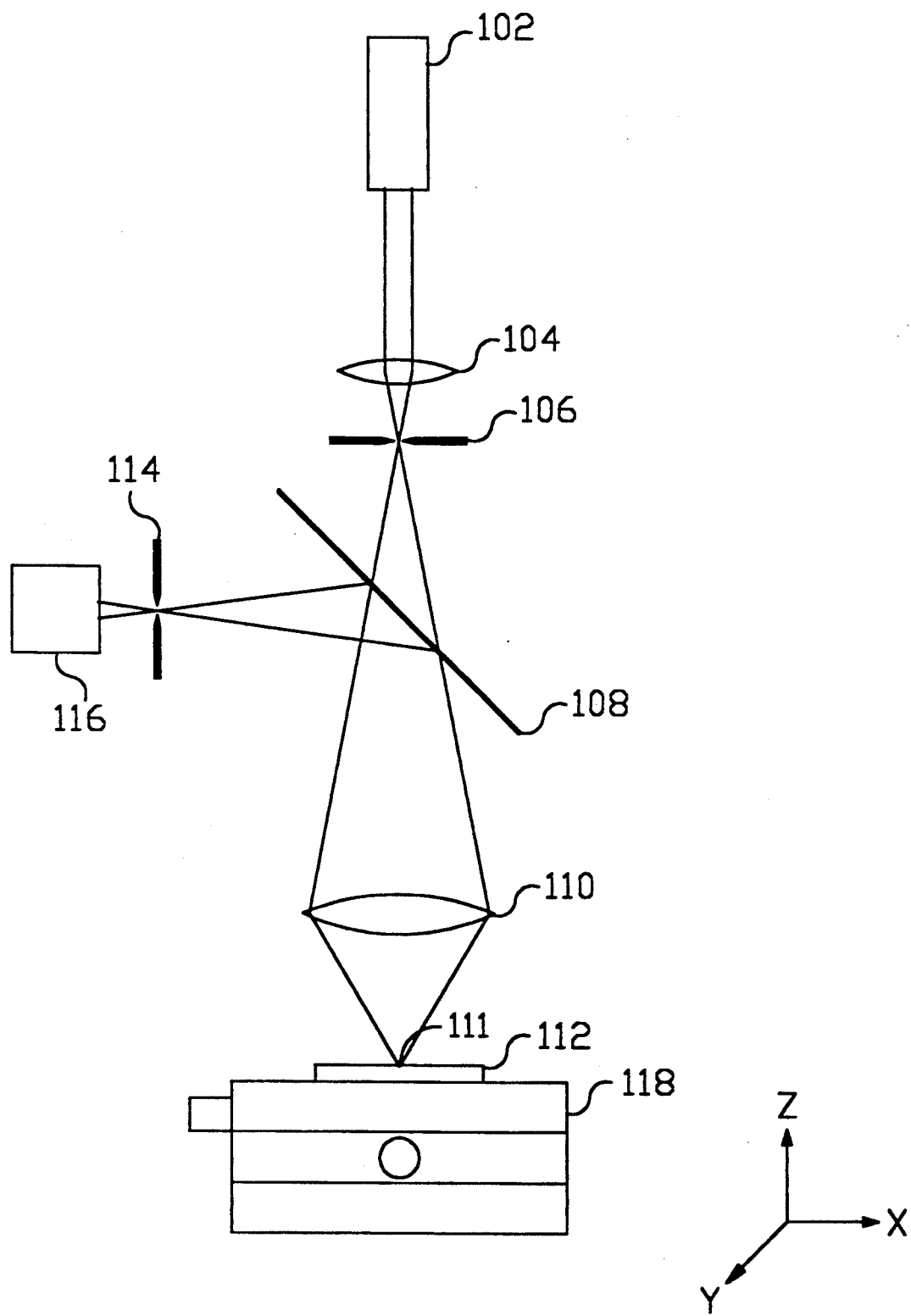
FIG. 1 is a simplified side view of a scanning stage confocal microscope of the prior art.
Figure 2:
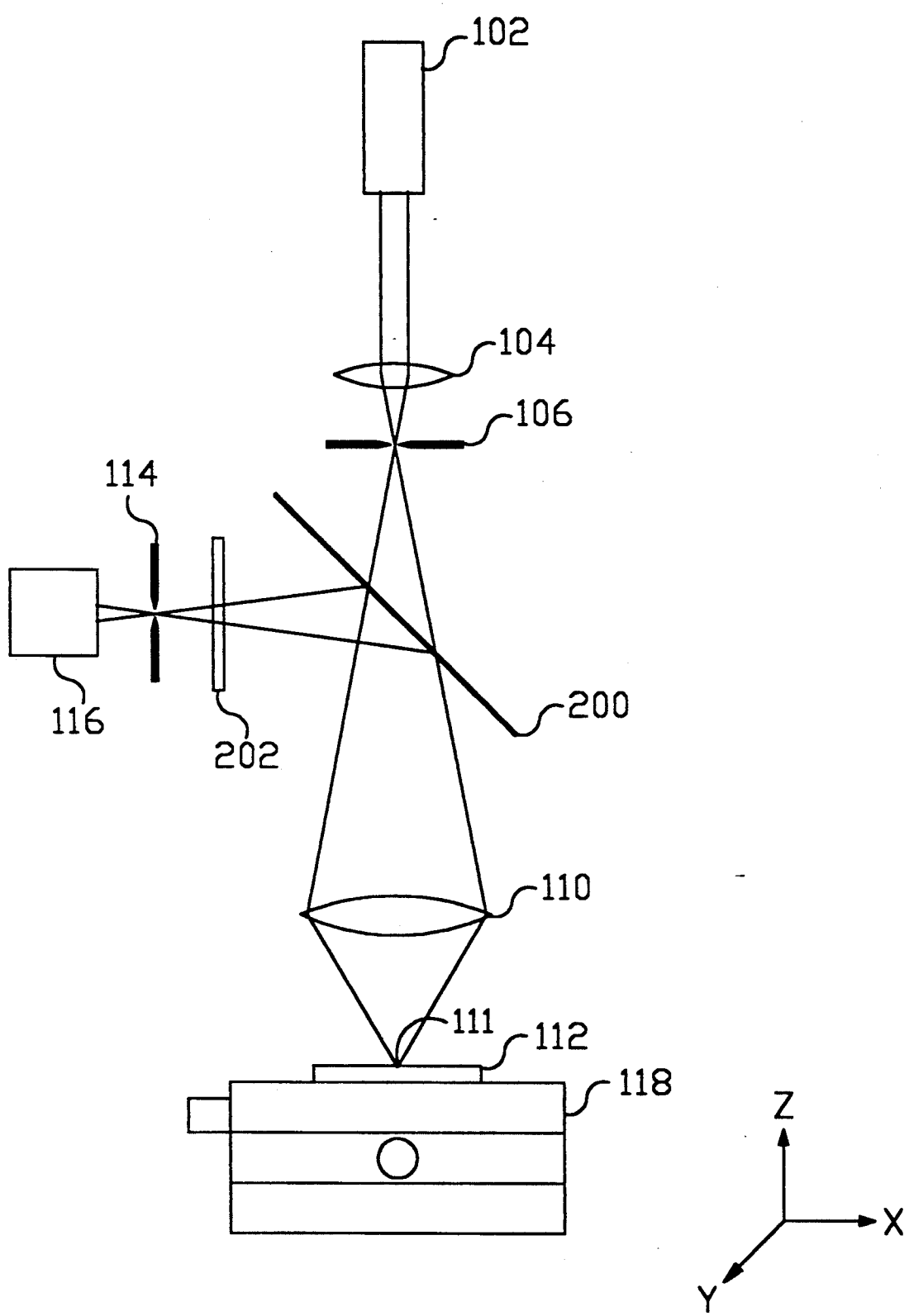
FIG. 2 is a simplified side view of a scanning stage confocal fluorescence microscope of the prior art.
Figure 3:
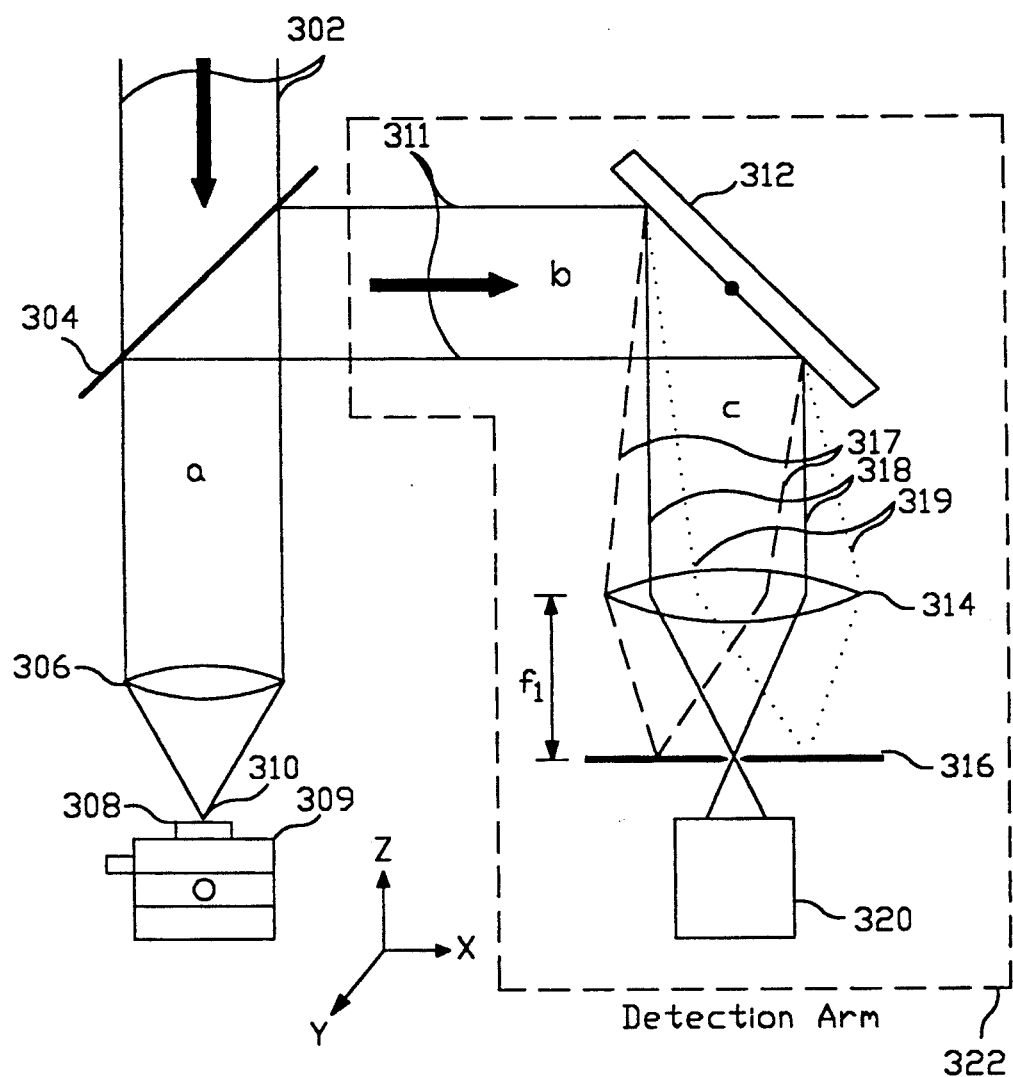
FIG. 3 shows a simple embodiment of the present invention in an infinity-corrected scanning stage confocal microscope (simplified side view).

FIG. 3 shows an infinity-corrected scanning stage confocal scanning laser microscope in which the spectrally-resolved detection system is implemented. In this embodiment, an incoming parallel beam 302 of laser light (or light from some other source, not shown) passes through beamsplitter 304 to enter objective lens 306, which focuses the beam to a small focal spot 310 at the surface of, or inside, specimen 308. In order to achieve the smallest possible focal spot, the incoming beam 302 has been expanded to fill objective lens 306, and a high quality, high numerical aperture (high NA)

lens (infinity-corrected in this example) is used for objective lens 306 so that a very small diffraction-limited spot (focal spot 310) will be formed. Light reflected back from (or emitted or scattered from) the region of the specimen enclosed in a small volume enclosing focal spot 310 is collected by objective lens 306, passes back up the microscope and is partially reflected by beamsplitter 304 into detection arm 322 of the microscope. This parallel beam 311 strikes diffraction grating 312 and is diffracted towards detector lens 314 of focal length $f_1$, placed a distance $f_1$ in front of detector pinhole 316. The diffraction grating 312 separates the incoming parallel beam 311 into its spectral components (three are shown in the diagram, 317, 318 and 319), and only a very narrow band of wavelengths (centered at the wavelength equivalent to beam 318 in the diagram), will pass through detector pinhole 316 to reach detector 320. For that narrow band of wavelengths, detector pinhole 316 is confocal with focal spot 310 at the focal point of objective lens 306, so the confocal properties of the microscope are preserved. In this embodiment, the three arms of the microscope (a, b and c) act like a grating monochromator, in which the illuminated focal spot 310 at the specimen position is the source of light entering the monochromator (and acts like the entrance slit of an ordinary grating monochromator), objective lens 306 focuses the light to a parallel beam which impinges on plane grating 312, and light at one wavelength (beam 318) is diffracted by the grating in exactly the correct direction to be focused on detector pinhole 316 by detector lens 314. Light at other wavelengths hits the area surrounding the pinhole, and is not detected. Detector pinhole 316 performs the function of the exit slit that would be used in an ordinary grating monochromator. A simple beam-expanding telescope can be used to adjust the diameter of the beam where it hits diffraction grating 312 (if required) and the diameter of the beam leaving the grating can be readjusted to fill detector lens 314 in front of detector pinhole 316 if necessary (beam shaping optics can also be added before and after diffraction grating 312 if necessary). All lenses in the return path of the beam should be achromatic over the range of wavelengths of interest, or alternatively reflecting optics can be used. Other optical combinations, which might include a concave grating, are also possible.

Figure 4:
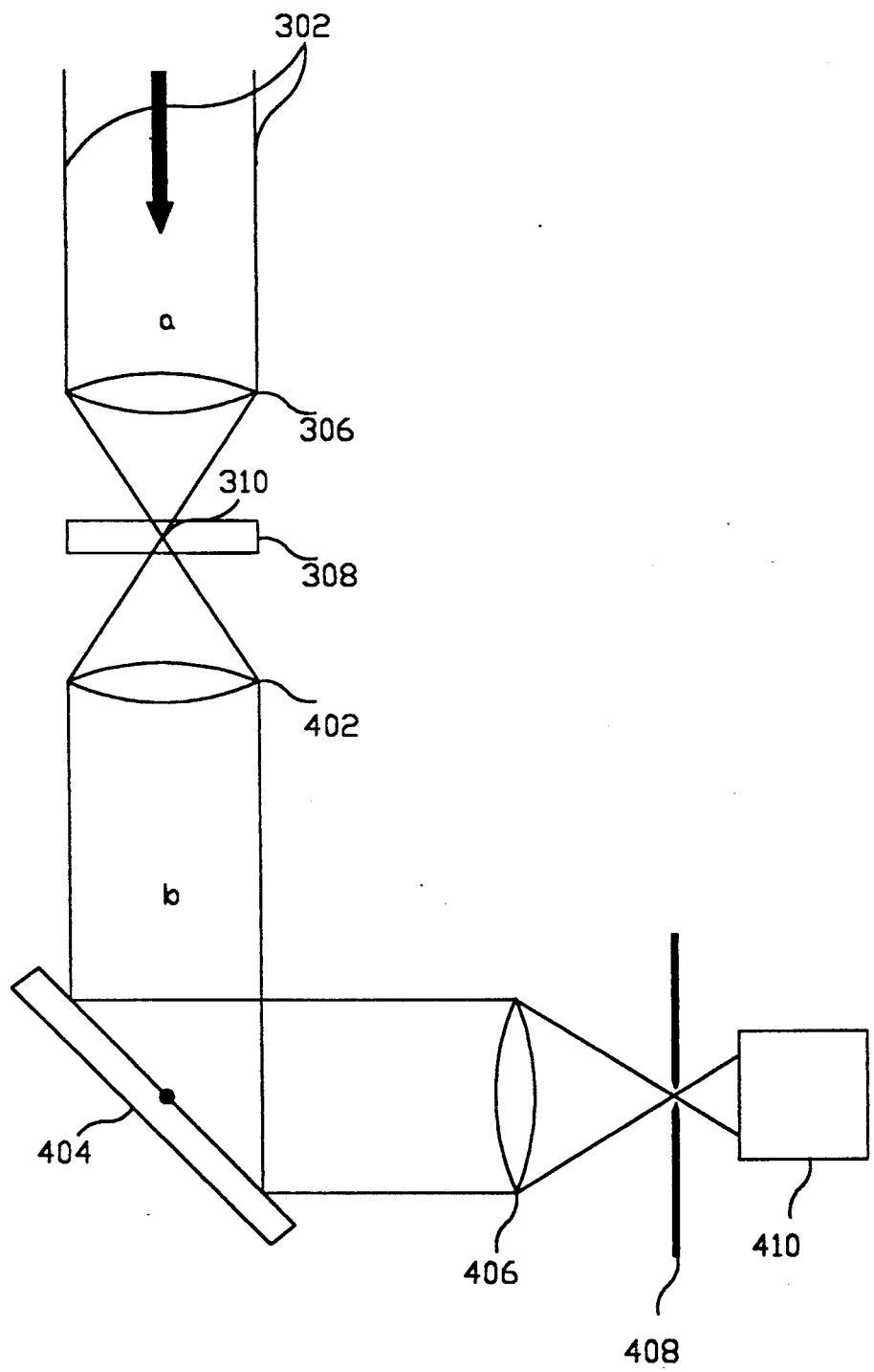
FIG. 4 shows a simplified side view of a scanning stage spectrally-resolved confocal transmission microscope.

FIG. 4 shows the spectrally-resolved detector integrated into a scanning stage confocal transmission microscope. In this embodiment, incoming parallel beam 302 (from a laser or other light source) is focused to a focal spot 310 at the surface of or inside specimen 308 by objective lens 306. Light transmitted through the specimen is collected by second objective lens 402, is then diffracted by diffraction grating 404, is focused by detector lens 406 and a small range of wavelengths passes through detector pinhole 408 and is detected by transmitted-light detector 410. Light of other wavelengths will not pass through pinhole 408 to be detected. In this embodiment objective lenses 306 and 402 are usually a matched pair of infinity-corrected microscope objectives, and the specimen is moved in a raster scan on translation stages (not shown).

Figures 5, 5A:
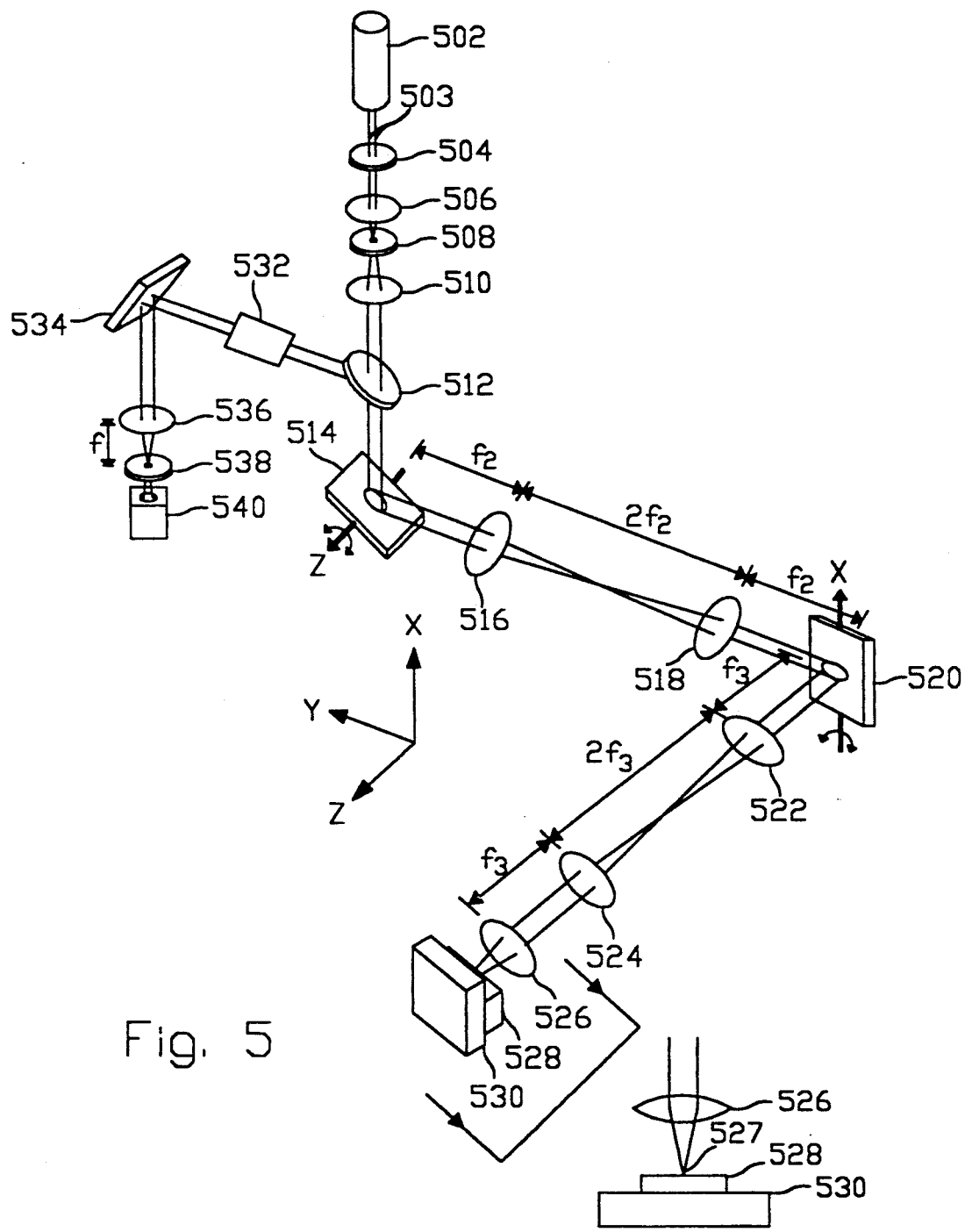
FIG. 5 is a simplified perspective view of a spectrally-resolved confocal scanning-beam optical microscope. This is the preferred embodiment of the present invention.
FIG. 5a is a simplified side view showing the specimen and focal spot of the microscope of FIG. 5.

FIG. 5 illustrates a further embodiment of the invention, the preferred embodiment, in which a grating monochromator has been integrated into the detection arm of a scanning beam confocal optical microscope. Light beam 503 from laser 502 (or other light source) passes through narrow bandpass filter 504 and is focused on pinhole 508 by lens 506. The expanding beam exiting pinhole 508 is focused to a parallel beam by lens 510. (Lens 506, pinhole 508 and lens 510 constitute a spatial filter and beam expander.) The parallel beam passes through beamsplitter 512 and is deflected in the x-y plane by first scanning mirror 514, which rotates about an axis parallel to the z-direction. Lenses 516 and 518 of focal length $f_2$ return the deflected light beam to the center of second scanning mirror 520, which rotates about an axis parallel to the x-direction and imparts a deflection in the y-z plane. Lenses 522 and 524 of focal length $f_3$ return the deflected beam (which now has been deflected by both scanning mirrors) to enter objective lens 526 centered on its entrance pupil. Objective lens 526 focuses the light to a focal spot 527 (see FIG. 5a) at the surface of or inside specimen 528. The focus position is set by focus stage 530, which moves in the z-direction. Light reflected back from or emitted by the tiny volume of the specimen at focal spot 527 is collected by objective lens 526 and passes back through the scan system of the microscope. Part of this returning beam is reflected by beamsplitter 512 towards beam expander 532 (optional) and scanning grating 534. Scanning grating 534 diffracts light towards lens 536, and a small range of wavelengths will be focused by lens 536 to pass through detector pinhole 538 and will reach detector 540. Light with other wavelengths will hit the opaque surface around pinhole 538 and will not be detected.

Our invention (as disclosed in FIGS. 3, 4 and 5 and described above), has several advantages over simply focusing the light from the detector pinhole onto the entrance slit of a grating monochromator (or placing the monochromator so that its entrance slit replaces the detector pinhole). First, it is a much more efficient optical arrangement, allowing more light to reach the detector. All of the light entering the detection arm of the microscope reaches the diffraction grating, whereas in the other arrangement only a fraction of the light passes through the entrance slit of the monochromator. Second, it is a simpler optical configuration, since for best optical efficiency with the grating monochromator it would be necessary to match the input NA of the grating monochromator with the output from the microscope, and third, it results in a more compact and less expensive microscope or mapping system.

This microscope measures the intensity of light reflected or emitted from the specimen as a function of x,y,z and wavelength. Data can be collected by scanning the grating to record a full spectrum at each position on the specimen (wavelength scanning), or the grating can be held in a single position while the specimen (or beam) is moved in a raster scan, storing a complete raster scan at only one wavelength. Another raster scan can then be performed at the next grating position (next wavelength), and so on. Any combination of single or multiple point, line, area or volume scans in position can be performed, measuring the light intensity at a single wavelength, several discrete wavelengths, or over the whole range of wavelengths measurable with that grating.

Figure 6:
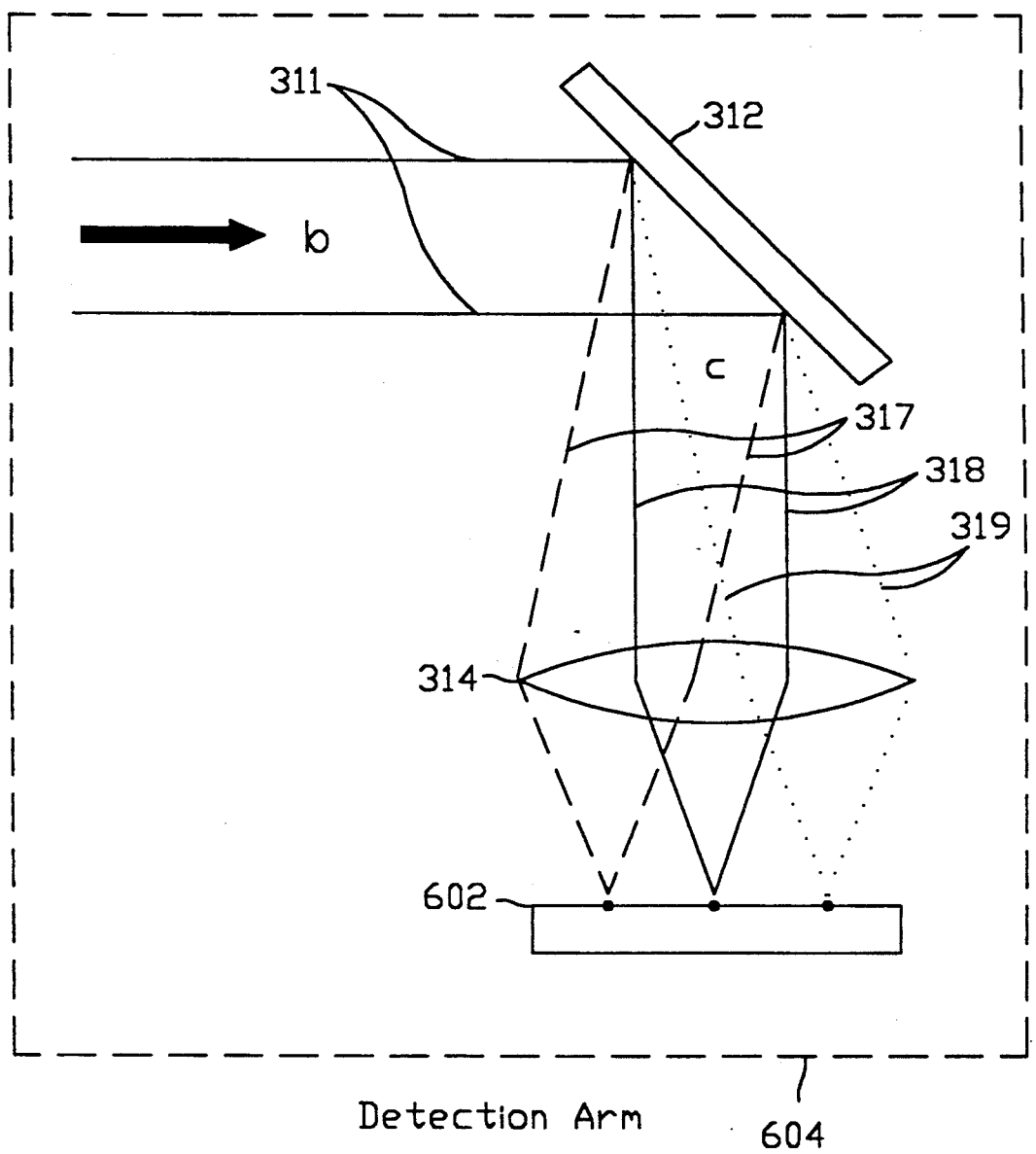
FIG. 6 is a simplified side view of a different embodiment of the detection arm of a microscope like the microscope shown in FIG. 3 or FIG. 5.

A further embodiment of the detection arm of the microscope (outlined with dashes in FIG. 3) is shown as detection arm 604 in FIG. 6. Here detector pinhole 316 and detector 320 (or single small detector) are replaced by a linear array 602 of $N_1$ small detectors. (In the figure, $N_1 = 3$.) This enables the microscope to simultaneously measure $N_1$ different wavelengths without scanning the grating.

Other optical arrangements may be appropriate in special situations, e.g. detector pinhole 316 (shown in FIG. 3) can be replaced by a slit parallel to the rulings on the grating, and in such a case it may be appropriate to use an evenly-illuminated slit in place of the pinhole in the spatial filter, resulting in a slit-shaped illuminated spot on the specimen. This slit should be fabricated with a width that is about the same as the diameter of the original spatial filter pinhole, so that the bright area on the specimen is as narrow as possible for good spectral resolution (since this slit image acts just like the real slit at the entrance of a grating monochromator), and should be oriented so that its image on the grating is oriented with its long dimension parallel to the rulings on the grating. In this kind of slit-scanning microscope, the specimen (or beam) is scanned in a direction parallel to the short dimension of the image of the rectangular slit at the specimen position. Scanning slit microscopes have some confocal qualities, and are described in the literature by Wilson, "The Role of the Pinhole in Confocal Imaging Systems", in "The Handbook of Biological Confocal Microscopy", edited by Pawley.

Figure 7:
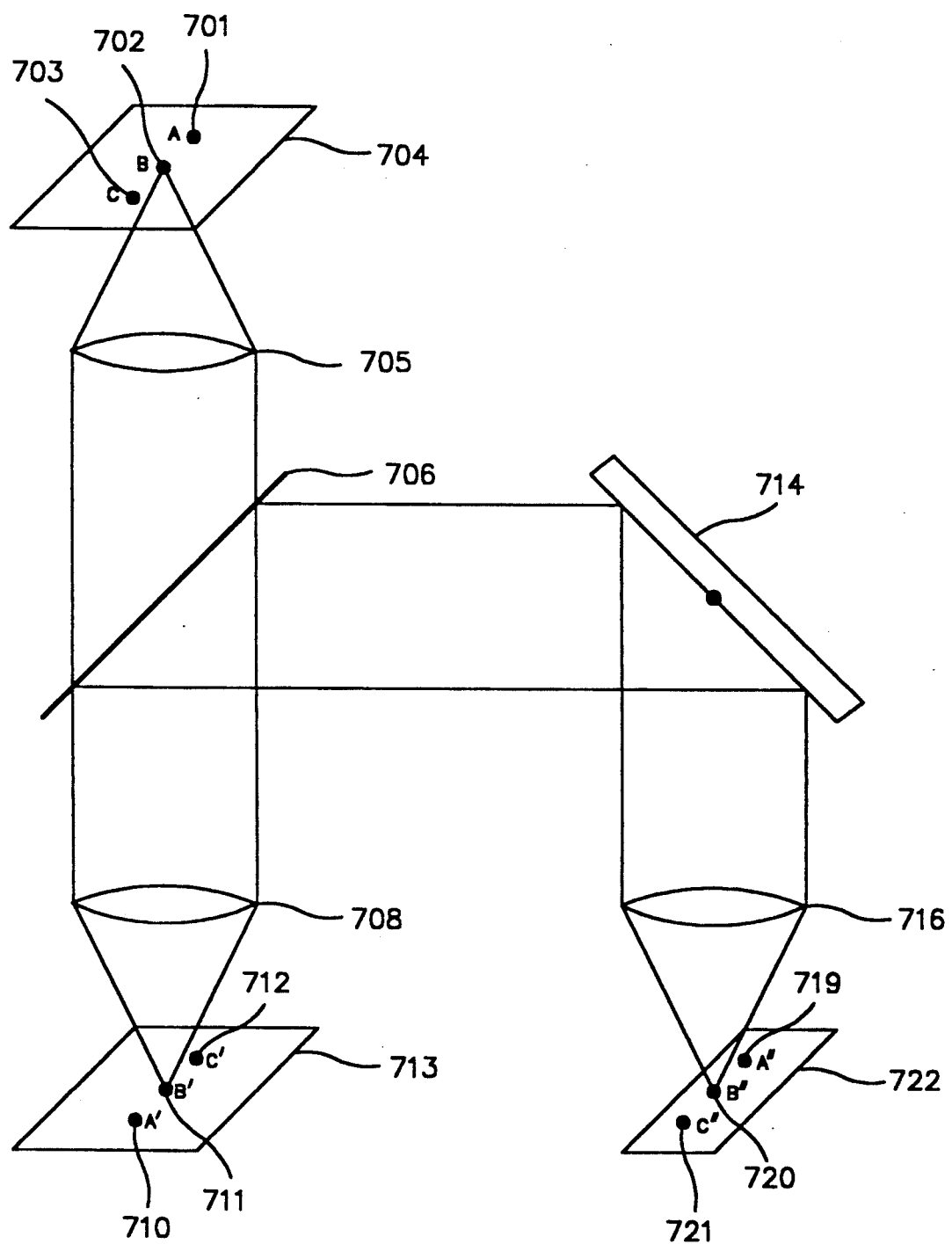
FIG. 7 is a further embodiment of the present invention in which a linear array of pinholes are illuminated at the top of the microscope to produce a linear array of focal spots on the specimen, which in turn produce a linear array of spectra at the position of a linear array of detectors.

A further possible arrangement would be to replace the pinhole at the spatial filter position by a linear array of pinholes illuminated with equal intensity, and then to focus these to a linear array of bright spots in the focal plane of the instrument (see FIG. 7). A linear array of small detectors 722, placed in confocal positions parallel to the direction of rulings on diffraction grating 714, allows the microscope to collect data from several positions on the specimen simultaneously when the specimen (or beam) is scanned in a direction perpendicular to the line of bright spots. If the linear detector array is replaced by a two-dimensional array with the same array spacing as just described above in the direction parallel to the ruling direction on the grating, then a spectral range can be collected from each spot as it scans across the specimen.

In all of the embodiments described so far, the illuminated focal spot acted like the entrance slit of the grating monochromator that has been integrated into the microscope, and it was therefore necessary to excite or illuminate the specimen with a focused beam of radiation. In the two embodiments described next, an entrance slit or pinhole is not required for the monochromator, and it is not necessary to illuminate or excite the specimen with a focused beam.

Figure 8:
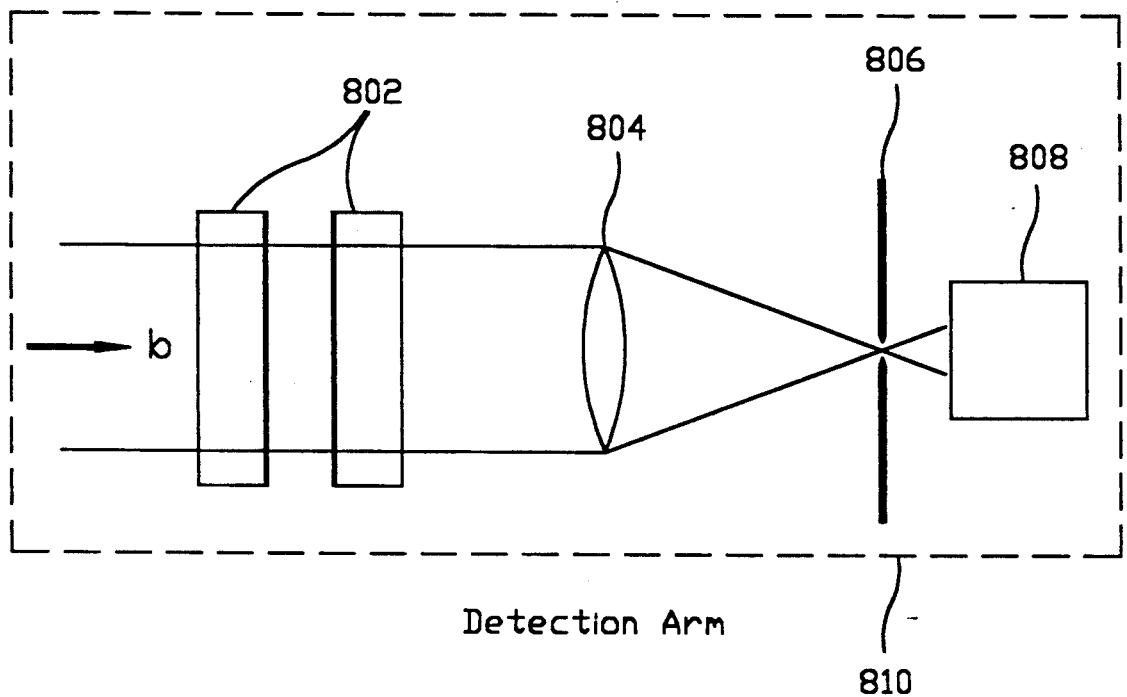
FIG. 8 is a simplified side view of another implementation of a detection arm of a microscope like the microscope shown in FIG. 3 or FIG. 5. This implementation incorporates a Fabry Perot interferometer.

FIG. 8 shows a further embodiment of a detection arm 810 that can replace detection arm 322 shown in FIG. 3. In FIG. 8, the grating has been replaced by Fabry-Perot interferometer 802. In this case a bandpass filter set is often used in front of the interferometer (at position b) to limit the range of wavelengths entering the interferometer to the range that it was designed to measure. The monochromatic light leaving the interferometer is then focused onto pinhole 806 (or small detector) by lens 804. Only light originating from a tiny volume around the focal point of the objective lens of the microscope (see FIG. 3) will be focused On pinhole 806, so this is a confocal microscope. Light originating from all other points in the specimen will be blocked by the metal surrounding pinhole 806. The microscope can be used in two different data collection modes. If the spacing of the interferometer plates is kept constant, a raster scan across the specimen allows data to be collected at a single wavelength. The spacing of the interferometer plates can then be changed to let a second wavelength through, and the raster scan repeated. This sequence is repeated until the required spectral information is collected at each scan position. In the second data collection mode, the measurement position is held fixed (by holding the specimen in a fixed position in a stage-scanning microscope, or by holding the beam-scanning components fixed in a beam-scanning microscope) while the complete spectrum is measured by varying the distance between plates in Fabry-Perot interferometer 802. The specimen or beam is then moved to the next position, and the spectrum is measured at that position, and so on until spectral information has been measured at each position in the raster scan. We contemplate using the Fabry-Perot interferometer to enable spectrally resolved measurements in yet a further class of scanning optical microscope, the Nipkow Disk microscope described by Kino in "Efficiency in Nipkow Disk Microscopes", an article in "The Handbook of Biological Confocal Microscopy", edited by Pawley.

Both of the embodiments described in FIGS. 3 and 8 are also very useful for fluorescence or photoluminescence lifetime experiments. In these experiments, two or more lifetimes are often measured simultaneously, making it difficult to separate the signals, especially if the measured lifetimes have nearly the same value. If different sources of photoluminescence or fluorescence are involved, they will likely emit radiation with different spectral components, so it is now possible to separate lifetimes from different sources (e.g. different fluorophores) by performing a lifetime measurement at different wavelengths, which not only separates the different lifetimes, but also helps identify the source of the signal. In these measurements the lifetime is measured at a single wavelength at each sample position, the detection wavelength is then changed, a second measurement is performed, and so on.

Figure 9:
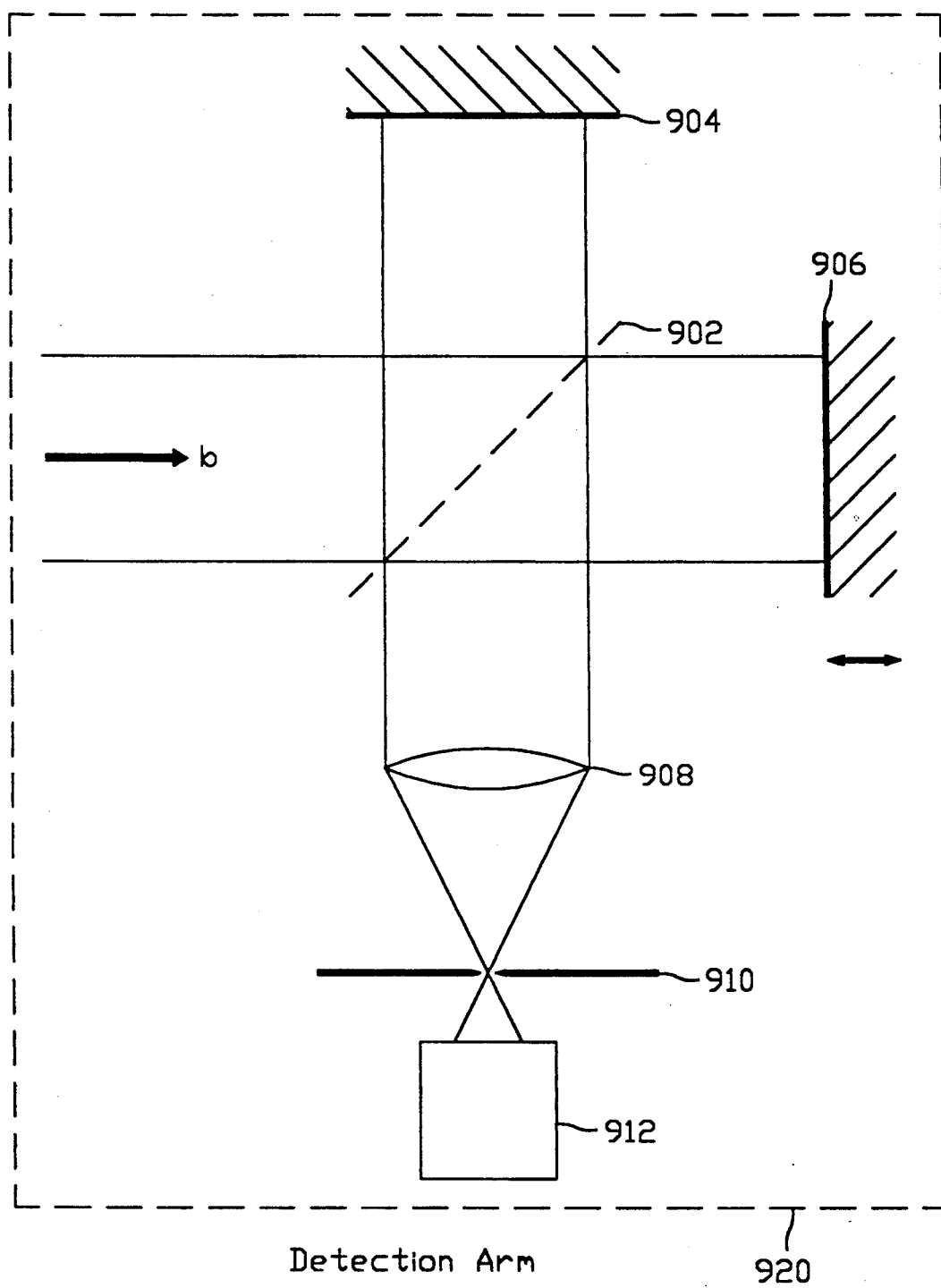
FIG. 9 is a simplified side view of yet another implementation of a detection arm of a microscope like the microscope shown in FIG. 3 or FIG. 5. This implementation incorporates a Fourier Transform spectrometer.

In FIG. 9, the detection arm 322 of the microscope shown in FIG. 3 has been replaced by a new detection arm 920 containing a two-arm (or two-beam) interferometer composed of beamsplitter 902, fixed mirror 904 and movable mirror 906, detector lens 908 to focus the light onto pinhole 910, and detector 912 to detect the light transmitted through pinhole 910. With its associated electronics, this forms the basis of a Fourier Transform (FT) spectrometer. In an ordinary FT spectrometer, light leaving the spectrometer is focused with a simple collector lens onto a detector which has an area that is much bigger than the pinhole used in this embodiment, and it is the addition of detector lens 908 and pinhole 910 that allows the FT spectrometer to be integrated into the detection arm of a confocal microscope, since the pinhole blocks light coming from any position in the specimen except from a tiny volume around the focal point of the microscope's objective lens. Since a Fourier Transform spectrometer measures a spectrum each time the movable mirror 906 is scanned, and cannot measure only one wavelength at a time, in this particular embodiment of the scanning laser microscope, a spectrum must be measured at each pixel position, so this embodiment is not appropriate for lifetime measurements.

The light source shown in all of the microscopes described is a laser, however other light or radiation sources can also be used.

Having described preferred embodiments of the new and improved spectrally-resolved scanning optical microscope or mapping system constructed in accordance with the present invention, it is believed that other modifications, variations, and changes will be suggested to those skilled in the art in view of the teachings set forth herein. It is therefore to be understood that all such variations, modifications and changes are believed to fall within the scope of the present invention as defined by the appended claims.

We claim:

1. A confocal scanning beam optical microscope for spectrally-resolved measurements comprising
   means for supporting a specimen to be observed and measured,
   an illumination source producing a light beam directed along an optical path toward said specimen,
   means for focusing the light beam to a diffraction-limited spot in a prescribed specimen plane,
   means for scanning the light beam to move the diffraction-limited spot in a predetermined scan pattern on said specimen plane,
   a detection arm receiving light reflected, scattered or emitted from said diffraction-limited spot in said specimen plane comprising
     a pinhole and a focusing lens for obtaining a focal point for confocal detection of the light returning from said specimen,
     a detector placed behind said pinhole,
     means for spectrally resolving said reflected, scattered or emitted light passing from said specimen back toward said focusing lens, pinhole and detector,
   a beamsplitter reflecting light returning from said specimen into said detection arm,
   wherein said spectrally-resolving means in said detection arm is selected from the group consisting of diffraction gratings and prisms that can be rotated to direct light of various wavelengths towards said focusing lens, whereby the diffraction-limited spot at the specimen acts like the entrance aperture of an integrated monochromator, and the pinhole in front of the detector acts like its exit aperture,
   means for measuring the intensity distribution with respect to wavelength of said reflected, scattered or emitted light.

2. A confocal scanning beam optical microscope for spectrally-resolved measurements comprising
   means for supporting a specimen to be observed and measured,
   an illumination source producing a light beam directed along an optical path toward said specimen,
   means for focusing the light beam to a diffraction-limited spot in a prescribed specimen plane,
   means for scanning the light beam to move the diffraction-limited spot in a predetermined scan pattern on said specimen plane,
   a detection arm receiving light reflected, scattered or emitted from said diffraction-limited spot in said specimen plane comprising
     a pinhole and a focusing lens for obtaining a focal point for confocal detection of the light returning from said specimen,
     a detector placed behind said pinhole,
     means for spectrally resolving said reflected, scattered or emitted light passing from said specimen back toward said second focusing lens, pinhole and detector,
   a beamsplitter reflecting light returning from said specimen into said detection arm,
   wherein said spectrally-resolving means in said detection arm is selected from the group consisting of Fabry-Perot interferometers and Fourier Transform spectrometers,
   means for measuring the intensity distribution with respect to wavelength of said reflected, scattered or emitted light.

3. A confocal scanning stage optical microscope for spectrally-resolved measurements comprising
   means for supporting a specimen to be observed and measured,
   an illumination source producing a light beam directed along an optical path toward said specimen,
   means for focusing the light beam to a diffraction-limited spot in a prescribed specimen plane,
   means for translating the specimen such that said diffraction-limited spot moves relative to the specimen in a raster scan confined to said prescribed specimen plane,
   a detection arm receiving light reflected, scattered or emitted from said diffraction-limited spot in said specimen plane comprising
     a pinhole and a focusing lens for obtaining a focal point for confocal detection of the light returning from said specimen,
     a detector placed behind said pinhole,
     means for spectrally resolving said reflected, scattered or emitted light passing from said specimen back toward said focusing lens, pinhole and detector,
   a beamsplitter reflecting light returning from said specimen into said detection arm,
   wherein said spectrally-resolving means in said detection arm is selected from the group consisting of diffraction gratings and prisms that can be rotated to direct light of various wavelengths towards said focusing lens, whereby the diffraction-limited spot at the specimen acts like the entrance aperture of an integrated monochromator, and the pinhole in front of the detector acts like its exit aperture,
   means for measuring the intensity distribution with respect to wavelength of said reflected, scattered or emitted light.

4. A confocal scanning stage optical microscope for spectrally-resolved measurements comprising
   means for supporting a specimen to be observed and measured,
   an illumination source producing a light beam directed along an optical path toward said specimen,
   means for focusing the light beam to a diffraction-limited spot in a prescribed specimen plane,
   means for translating the specimen such that said diffraction-limited spot moves relative to the specimen in a raster scan confined to said prescribed specimen plane,
   a detection arm receiving light reflected, scattered or emitted from said diffraction-limited spot in said specimen plane comprising
     a pinhole and a focusing lens for obtaining a focal point for confocal detection of the light returning from said specimen,
     a detector placed behind said pinhole,
     means for spectrally resolving said reflected, scattered or emitted light passing from said specimen back toward said focusing lens, pinhole and detector,
   a beamsplitter reflecting light returning from said specimen into said detection arm, wherein said spectrally-resolving means in said detection arm is selected from the group consisting of Fabry-Perot interferometers and Fourier Transform spectrometers, means for measuring the intensity distribution with respect to wavelength of said reflected, scattered or emitted light.

5. A scanning beam optical microscope or mapping system for spectrally-resolved measurements comprising means for supporting a specimen to be observed and measured, an illumination source producing a light beam directed along an optical path toward said specimen, means for focusing the light beam to an illuminated spot in a prescribed specimen plane, means for scanning the light beam to move said illuminated spot in a predetermined scan pattern on said specimen plane, a detection arm receiving light reflected, scattered or emitted from said illuminated spot in said specimen plane comprising
  an aperture and focusing lens,
  a detector placed behind said aperture,
  means for spectrally-resolving said reflected, scattered or emitted light passing form said illuminated spot in said specimen plane back towards said focusing lens, aperture and detector,
  a beamsplitter reflecting light returning from said specimen into said detection arm wherein said spectrally-resolving means in said detection arm is selected from the group consisting of diffraction gratings and prisms that can be rotated to direct light of various wavelengths towards said focusing lens, whereby the illuminated spot at the specimen acts like the entrance aperture of an integrated monochromator, and said aperture acts like its exit aperture, means for measuring the intensity distribution with respect to wavelength of said reflected, scattered or emitted light.

6. A scanning beam optical microscope or mapping system for spectrally-resolved measurements comprising means for supporting a specimen to be observed and measured, an illumination source producing a light beam directed along an optical path toward said specimen, means for focusing the light beam to an illuminated spot in a prescribed specimen plane, means for scanning the light beam to move said illuminated spot in a predetermined scan pattern on said specimen plane, a detection arm receiving light reflected, scattered or emitted from said illuminated spot in said specimen plane comprising
  an aperture and focusing lens,
  a detector placed behind said aperture,
  means for spectrally-resolving said reflected, scattered or emitted light passing from said illuminated spot in said specimen plane back towards said focusing lens, aperture and detector,
  a beamsplitter reflecting light returning from said specimen into said detection arm wherein said spectrally-resolving means in said detection arm is selected from the group consisting of Fabry-Perot interferometers and Fourier Transform spectrometers, means for measuring the intensity distribution with respect to wavelength of said reflected, scattered or emitted light.

7. A scanning stage optical microscope or mapping system for spectrally-resolved measurements comprising means for supporting a specimen to be observed and measured, an illumination source producing a light beam directed along an optical path toward said specimen, means for focusing the light beam to an illuminated spot in a prescribed specimen plane, means for translating the specimen such that said illuminated spot moves relative to the specimen in a raster scan in the prescribed specimen plane, a detection arm receiving light reflected, scattered or emitted from said illuminated spot in said specimen plane comprising
  an aperture and focusing lens,
  a detector placed behind said aperture,
  means for spectrally-resolving said reflected, scattered or emitted light passing from said illuminated spot in said specimen plane back towards said focusing lens, aperture and detector,
  a beamsplitter reflecting light returning from said specimen into said detection arm wherein said spectrally-resolving means in said detection arm is selected from the group consisting of Fabry-Perot interferometers and Fourier Transform spectrometers, means for measuring the intensity distribution with respect to wavelength of said reflected, scattered or emitted light.

8. A scanning stage optical microscope or mapping system for spectrally-resolved measurements comprising means for supporting a specimen to be observed and measured, an illumination source producing a light beam directed along an optical path toward said specimen, means for focusing the light beam to an illuminated spot in a prescribed specimen plane, means for translating the specimen such that said illuminated spot moves relative to the specimen in a raster scan in the prescribed specimen plane, a detection arm receiving light reflected, scattered or emitted from said illuminated spot in said specimen plane comprising
  an aperture and focusing lens,
  a detector placed behind said aperture,
  means for spectrally-resolving said reflected, scattered or emitted light passing from said illuminated spot in said specimen plane back towards said focusing lens, aperture and detector,
  a beamsplitter reflecting light returning from said specimen into said detection arm wherein said spectrally-resolving means in said detection arm is selected from the group consisting of diffraction gratings and prisms that can be rotated to direct light of various wavelengths towards said focusing lens, whereby the illuminated spot at the specimen acts like the entrance aperture of an integrated monochromator, and said aperture acts like its exit aperture, means for measuring the intensity distribution with respect to wavelength of said reflected, scattered or emitted light.

* * * * *